United States Patent
Kormann et al.

(10) Patent No.: US 7,804,588 B2
(45) Date of Patent: Sep. 28, 2010

(54) MEASURING DEVICE FOR OPTICAL AND SPECTROSCOPIC EXAMINATION OF A SAMPLE

(75) Inventors: Georg Kormann, Urbandale, IA (US); Rico Priesnitz, Lebach (DE); Nico Correns, Weimar (DE); Michael Rode, Jana (DE)

(73) Assignee: Deere & Company, Moline, IL (US)

( * ) Notice: Subject to any disclaimer, the term of this patent is extended or adjusted under 35 U.S.C. 154(b) by 0 days.

(21) Appl. No.: 11/972,104

(22) Filed: Jan. 10, 2008

(65) Prior Publication Data

US 2008/0186487 A1    Aug. 7, 2008

(30) Foreign Application Priority Data

Feb. 7, 2007 (DE) .................. 10 2007 007 040

(51) Int. Cl.
  *G01J 3/10* (2006.01)
  *G01J 3/42* (2006.01)
(52) U.S. Cl. ............................ 356/72; 356/328; 356/634
(58) Field of Classification Search ................. 356/326, 356/328
  See application file for complete search history.

(56) References Cited

U.S. PATENT DOCUMENTS

| | | |
|---|---|---|
| 5,510,619 A | 4/1996 | Zachmann et al. |
| 6,119,442 A | 9/2000 | Hale |
| 6,421,990 B1 | 7/2002 | Ohlemeyer et al. |
| 7,265,831 B2 | 9/2007 | Kormann et al. |

FOREIGN PATENT DOCUMENTS

| | | |
|---|---|---|
| DE | 44 14 622 A1 | 10/1995 |
| DE | 4414622 | 10/1995 |
| DE | 19717885 | 11/1997 |
| DE | 19922867 | 11/2000 |
| DE | 2020050 01 438 U1 | 5/2005 |
| DE | 202005001438 | 6/2005 |
| DE | 102004048103 | 4/2006 |
| EP | 1 486 769 | 12/2004 |
| EP | 1 522 214 | 4/2005 |
| EP | 1 671 530 | 6/2006 |
| EP | 1671530 | 6/2006 |
| FR | 2881522 | 8/2006 |
| GB | 2 284 477 | 6/1995 |
| WO | WO-00/08448 | 2/2000 |
| WO | 2006010761 | 2/2006 |

OTHER PUBLICATIONS

English Translation of DE 20 2005 001 438 U1 (publication date—Jun. 9, 2005).*
European Search Report for European Application No. 08100924.3 dated Oct. 6, 2009.

* cited by examiner

*Primary Examiner*—F. L Evans
(74) *Attorney, Agent, or Firm*—Foley & Lardner LLP (57) ABSTRACT

A measuring device for optical and spectroscopic examination of a sample includes a housing, a first light source, a window, an optical spectrometer with a dispersive element and a number of detector elements and which can record light from the first light source which is indirectly reflected by the sample and reenters the housing through the window, an electronic camera whose incidence opening is directed onto the sample, through the window, and an electronic evaluation device which is connected to an image sensor of the camera and to the detector elements. The camera may be assigned a second light source.

12 Claims, 5 Drawing Sheets

MEASURING DEVICE FOR OPTICAL AND SPECTROSCOPIC EXAMINATION OF A SAMPLE

This application claims priority based on German Application No. 102007007040.5, filed on Feb. 7, 2007, which is hereby incorporated by reference in to this application.

FIELD OF THE INVENTION

The invention relates to a measuring device for optical and spectroscopic examination of a sample.

BACKGROUND OF THE INVENTION

The prior art describes various measuring devices serving the purpose of examining any desired materials optically. Such measuring devices are used, inter alia, in agriculture in order to classify harvest material, and in the food industry for the purpose of characterizing and monitoring raw materials. Measuring devices based on spectroscopic methods and/or on an optical detection of the samples (with the use of image processing systems) have been described:

DE 199 22 867 A and DE 10 2004 048 103 A describe spectroscopic measuring devices for agricultural harvesting machines which comprise a light source which radiates the sample, in particular harvest material, with a light during operation. Light reflected by the sample is deflected in a spectrometer in different directions dependent on wavelength by a dispersive element for example a grating or a prism. Detector elements receive the light, which is now assigned to known wavelengths and whose wavelengths lie in the visible wavelength region or in the near infrared region. The output signals of the detector elements are fed to an evaluation device which calculates specific parameters of the sample with the aid of the measured spectra.

Measuring devices which are based on an optical detection of the samples and use image processing systems have been described in U.S. Pat. No. 6,119,442 A, WO 2006/010761 A and EP 1 671 530 A. The sample is irradiated with light and the reflected light is detected by a camera. In accordance with U.S. Pat. No. 6,119,442 A, for example, after an image analysis by means of the image processing system information is available relating to the brokens content in the threshed grain of a combine harvester after passage through the threshing device, and/or relating to the fraction of the impurities in the cleaned grain after passage of the cleaning device, and is used for the automatic setting of the concave gap and/or the speed of the cleaning fan. In the case of a forage harvester, EP 1 671 530 A proposes to illuminate the chopped harvest material with a flash light and to examine it with a camera in order to evaluate the actual cut length.

DE 20 2005 001 438 U, which is regarded as generic, describes a measuring arrangement having a near infrared spectrometer and a camera which detects light indirectly reflected by the sample and which light originates from an incandescent lamp. The spectrometer and the camera are arranged inside a common housing and cooperate with the sample through a window. The combined evaluation of the data records of the spectrometer and of the image data records on the camera is intended to improve the accuracy of the measurements of the spectrometer for example in the spectroscopic measurement of the mineral content of flour while considering the appearance, the colour and the existing blackenings of the flour which are detected by the camera.

The sample is illuminated in DE 20 2005 001 438 U by a light source in the form of a halogen lamp. The light from the light source is used jointly by the camera and the spectrometer. Because of different wavelengths required by the spectrometer (near infrared region) and the camera (visible light), a very wideband light source is required which has a poor efficiency. Again, optimizing the light source for the wavelengths of the spectrometer or the camera would entail a worsening of the illumination in the wavelengths of the other sensor element. Furthermore, the light source operates continuously in the prior art, the result of this being that the camera requires a very short shutter speed in order to record relatively quickly moving samples sufficiently sharply.

Thus, there is a need for providing a measuring device that provides improved illumination of the sample.

BRIEF DESCRIPTION OF THE DRAWINGS

An exemplary embodiment of the invention which is described in more detail below is illustrated in the drawing, in which.

BRIEF DESCRIPTION OF THE PREFERRED EMBODIMENTS

The optical elements of a measuring device for optical and spectroscopic examination of a sample are arranged in a protected and compact fashion in a housing which has in a wall a transparent window in which a (window) pane transparent to light is arranged. Located inside the housing are a first light source, a second light source, a spectrometer operating, in particular, in the near infrared region and having a dispersive element and a number of detector elements, as well as a camera. An electronic evaluation device, which can be located in the housing or outside thereof, is connected to an image sensor of the electronic camera and to the detector elements in such a way that it transmits signals.

The first light source is assigned to the spectrometer. During measurement operation, the first light source radiates light onto the sample through the window. Light reflected indirectly by the sample then falls in turn through the window into the spectrometer and is decomposed there by the dispersive element into its wavelength fractions, which then fall onto the individual detector elements. The direct reflection from the sample and the window pane does not fall into the spectrometer; a classic dark-field illumination is therefore present.

Similarly, the second light source is assigned to the camera. During measurement operation, the second light source radiates light onto the sample through the window. Light indirectly reflected by the sample then falls, in turn, through the window into the incidence opening of the camera and is converted there into an image signal. The direct reflection from the sample and the window pane does not fall into the camera; a classic dark-field illumination is therefore likewise present.

The beam path of the spectrometer goes from the first light source through the window to the sample and back into the spectrometer. The beam path of the camera runs from the second light source via the window to the sample and back into the objective of the camera. Only in the region of the window and the sample are the two beam paths coincident. The areas of sharp focus for both beam paths are situated on the outer surface of the transparent pane or slightly displaced into the sample. Camera and spectrometer are arranged outside the specular angle, and this prevents corruption of the measurement results through direct reflection or gloss.

The spectrometer and the camera are in this way respectively assigned a dedicated light source which can be optimally adapted to the respective application.

In a preferred embodiment, the first light source and the spectrometer are situated diametrically opposite an optical axis of the window which is defined by the normal vector of the window pane. Similarly, the second light source and the camera are also situated diametrically opposite the optical axis of the window. The two light sources are arranged angularly offset from one another in relation to the optical axis of the window, as are also the camera and the spectrometer.

The second light source can preferably be operated in a pulsed operation, in order to be able to emit relatively short light flashes onto the sample, and to be able to image moving samples sharply even without a camera with high shutter speed. It is possible to this end to make use of a common gas discharge flash lamp or one or more (white or coloured) light-emitting diodes. The first light source, by contrast, preferably emits light continuously in operation and is, in particular, a halogen incandescent lamp.

The evaluation device which is connected, or can be connected, to the image sensor of the camera and the detector elements uses the output signals of the detector elements in order to determine specific parameters of the sample. These can be, for example, the content of constituent organic substances, of starch, enzyme-soluble organic substances, non-organic minerals such as, for example, sodium and magnesium (ash), raw protein, oil, water, dry substance, digestibility, energy content, raw fibre content and/or the fibre length of the sample. The signals of the camera are processed in the evaluation device by image processing software in order to determine other parameters of the sample such as size of the sample particles, their colour or a fraction of impurities. The sample parameters determined by the image processing software can also be used to check the parameters determined by means of the spectrometer and, for example, to be able to exclude implausible parameters or to correct the parameters determined. Thus, a parameter determined with the aid of a spectrum of a heavily contaminated sample can be rejected as useless. Again, a sample parameter determined by the image processing software can serve for correcting the parameters determined with the aid of the spectra, for example by identifying the fractions of the sample constituents on which the spectrum is based, and assigning the parameters obtained with the aid of the spectrum to the individual constituents. Thus, in the case of a combine harvester it is possible to undertake correction of the spectrometer data errors by using the data obtained from the image processing and relating to the brokens fraction and the impurities fraction. Similarly, the spectrometer spectra determined in assigning the image components can be used.

The electronic evaluation device can also use the image processing software to evaluate the length of particles of the sample by identifying and measuring the particle boundaries. Measuring the particle length is, in particular, useful for controlling cut length in a forage harvester. A possible limitation of the field of view of the camera can be circumvented in various ways by the size of the window:

In one possible variant, a statistical analysis is carried out and the evaluation device is fed information relating to the speed of movement of the particles and their size (that is to say thickness in the longitudinal direction). The evaluation device identifies cut edges in the image, which are identified by virtue of the fact that their dimension corresponds approximately to the size of the particle. The length of the particle is then determined with the aid of the number of visible cut edges, an item of information relating to the respective particle throughput and the speed which is fed to the evaluation device.

Another variant provides that the camera is a high speed camera with a one-dimensional or two-dimensional image sensor which can record groups of images in relatively fast sequence. Such a camera can record an image sequence in the case of which the contents of the images adjoin one another. Owing to this overlapping, a virtual image in the direction of movement of the particle can be produced in the evaluation device. The particle boundaries are identified and measured in this image in order to determine the particle length.

The inventive measuring device can be used in a stationary or mobile fashion to examine any desired samples. A preferred place of use is a self-propelled or drawn or mounted harvesting machine where the measuring device can examine a flow of harvest material, be this upstream or downstream of a harvest material pick-up device of the harvesting machine.

The measuring device can serve for georeferenced mapping of the determined parameters such that the latter can be used further for the purposes of precision agriculture. The parameters determined can, however, also be applied in controlling actuators of the harvesting machine, for example to use the measuring device to measure the cut length of harvest material chopped in a forage harvester, to compare it with the desired value, and to control the speed of a cut length gear of the forage harvester. Similarly, the measuring device can detect the brokens fraction downstream of a threshing device of a combine harvester and is control the size of the concave gap, or the fraction of impurities in the grain is detected at the grain elevator and used to control the fan speed for cleaning, and/or sieve opening.

Figure 1:
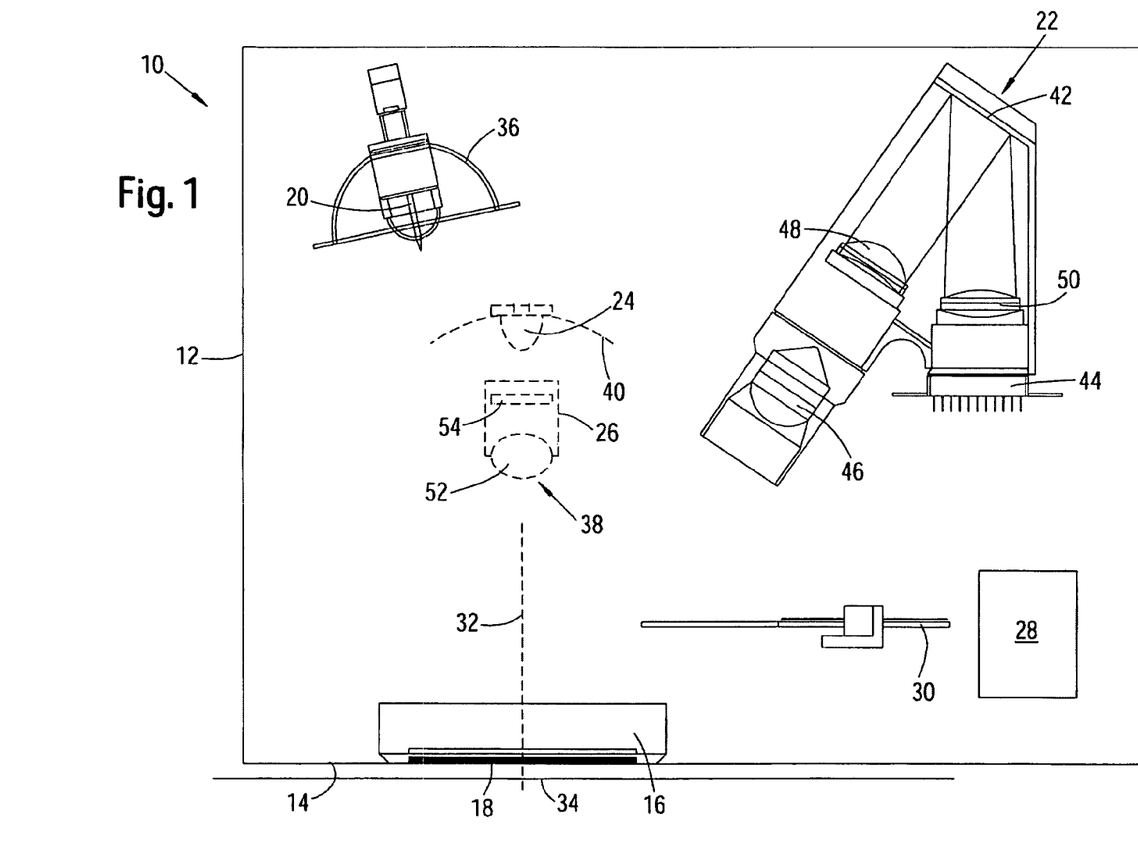
FIG. 1 shows a diagrammatic lateral view of an inventive measuring device for optical and spectroscopic examination of a sample.

FIG. 1 reproduces a measuring device 10 in a side view. The measuring device 10 comprises a housing 12 in whose wall depicted below there is arranged a window 16 in which there is incorporated a transparent, plane-parallel pane 18 made from sapphire glass or another, suitable material. Located inside the housing 12 are a first light source 20, a spectrometer 22, a second light source 24, an electronic camera 26, an evaluation device 28 and a calibration arrangement 30 for the spectrometer 22. The insides of the walls of the housing 12 can be blackened in order to avoid undesired reflections.

Figure 2:
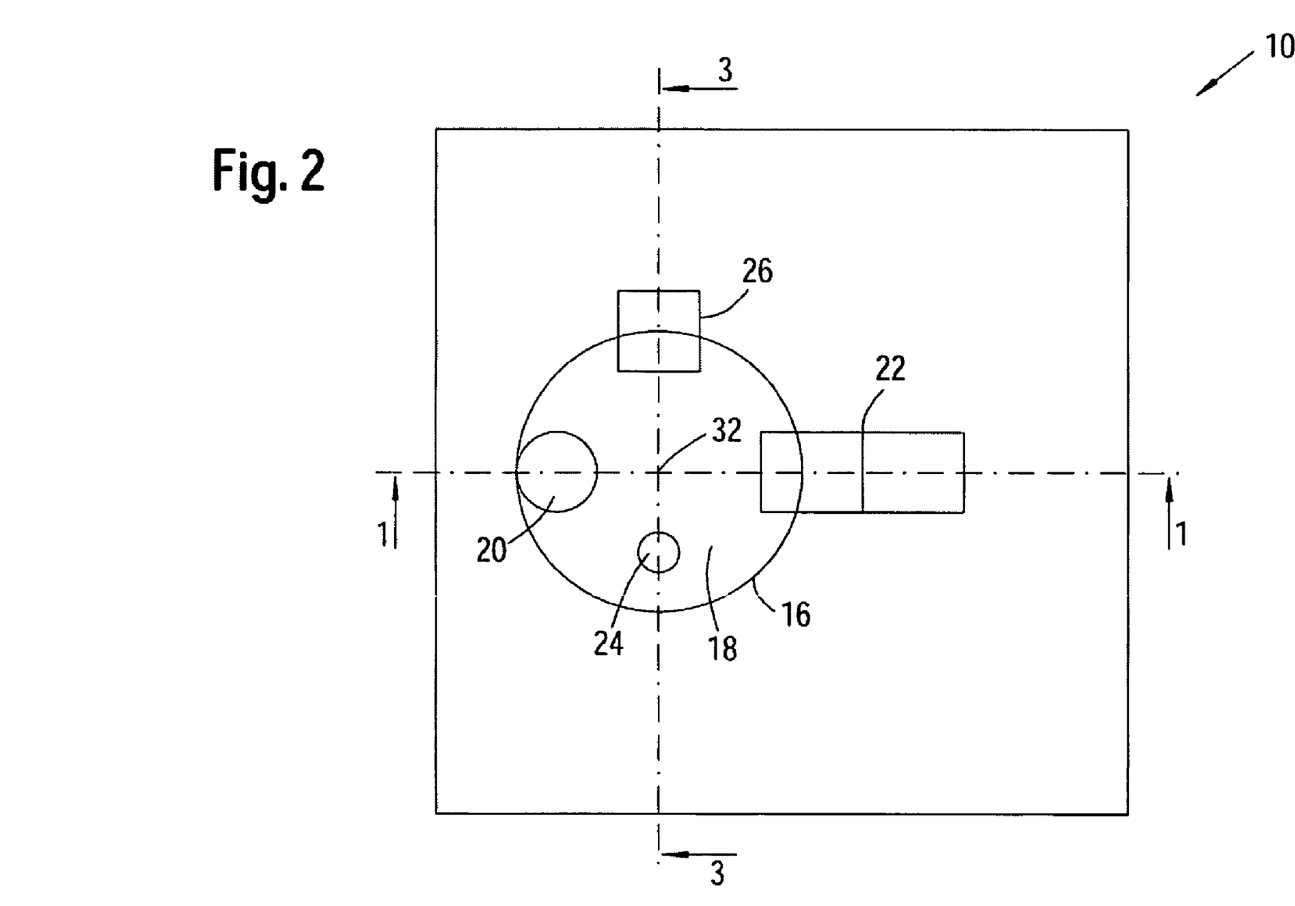
FIG. 2 shows a top view of the measuring device according to FIG. 1.
Figure 3:
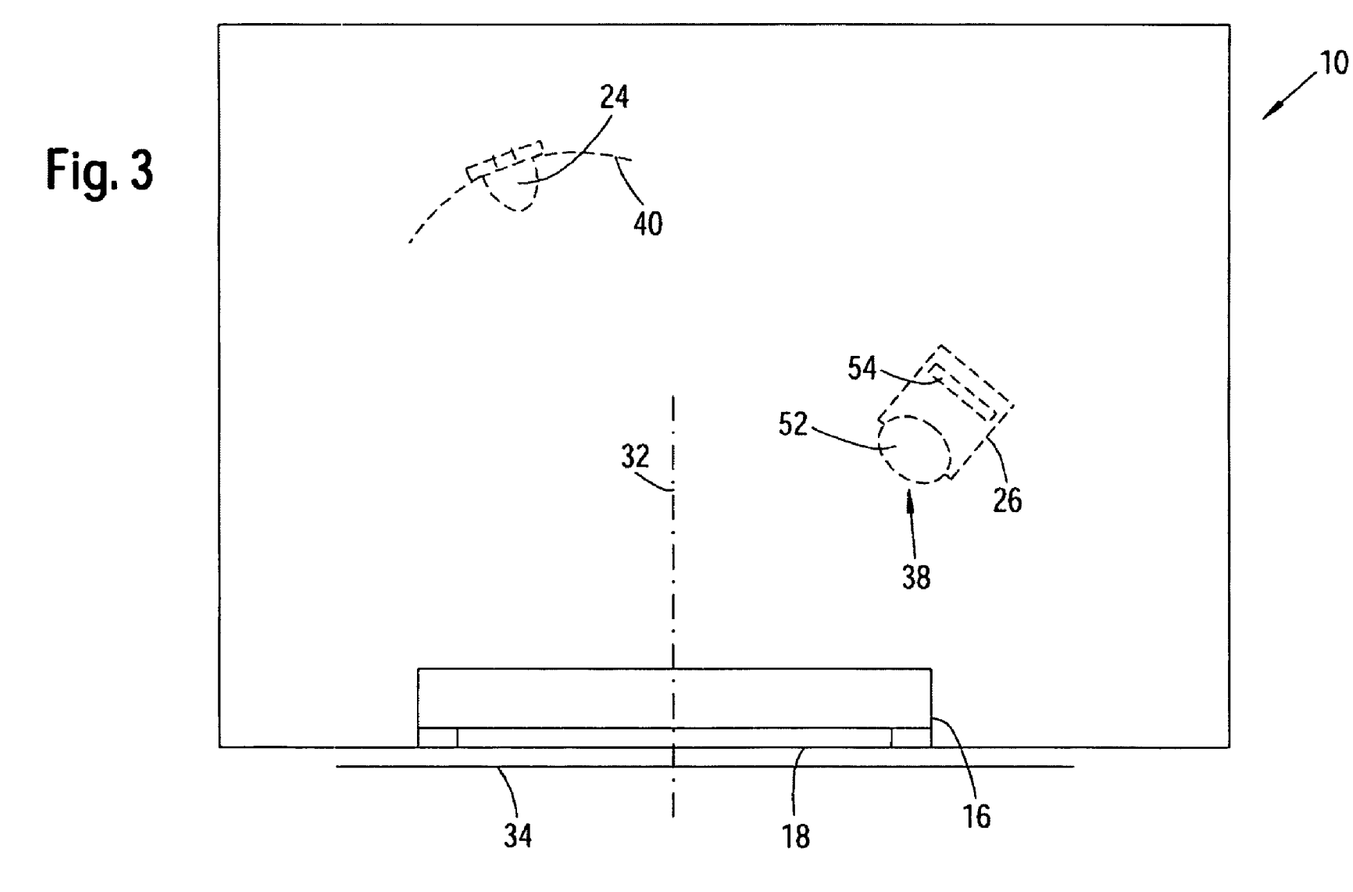
FIG. 3 shows a section through the measuring device of FIGS. 1 and 2 along the line 3-3 in FIG. 2.

The spatial arrangement of the optical components of the measuring device 10 are rendered plainer with the aid of FIGS. 2 and 3. The first light source 20 is arranged at an angle of approximately 10° to an optical axis 32 of the pane 18 of the window 16. As is to be seen with the aid of FIG. 2, the spectrometer 22 is diametrically opposite the first light source 20 in relation to the optical axis 32, and encloses a relatively large angle of approximately 30° with the optical axis 32. As may be seen from FIGS. 2 and 3, the second light source 24 and the camera 26 are also situated diametrically opposite in relation to the optical axis 32. The second light source 24 is arranged at an angle of approximately 10° in relation to the optical axis 32, while the camera 26 encloses a relatively large angle of approximately 30° with the optical axis 32. Fitting the camera 26 and spectrometer 22 outside the specular angle of the light sources 20, 24 precludes direct reflections at the pane 18 or at the sample 34, which is located directly below the pane 18, from penetrating into the camera 26 or into the spectrometer 22 and corrupting measurements or rendering them impossible through glare.

Imaginary connecting lines, lying in the plane of FIG. 2, between the camera 26 and the second light source 24, on the one hand, and between the spectrometer 22 and the first light source 20, on the other hand, enclose an angle of approximately 90°.

The light from the first light source 20, which is a continuously operated halogen lamp, falls in a fashion focused by a reflector 36 through the pane 18 onto the sample 34. Only the light reflected by the latter, indirectly, that is to say not at the specular angle, passes again through the pane 18 and into the spectrometer 22.

The spectrometer 22 comprises a dispersive element 42 in the form of a grating applied to a mirror, and a detector array with a number of detector elements 44, and has imaging optical assemblies 46, 48, 50. Owing to the direct imaging of the radiation reflected by the sample 34 onto the detector elements 44, imaging from the structure of the sample 34 onto the detector elements 44 can lead to measuring errors, depending on the sample 34. In order to prevent this, a light integrator can be provided for homogenization. The calibration device 30 serves for calibrating the spectrometer 22 and comprises a white and a black standard which can be moved by motor into the beam path between the first light source 20 and the spectrometer 22. The calibration device 30 is controlled by the evaluation device 28.

After being focused by a reflector 40, the light from the second light source 24, which can optionally be operated continuously or in pulsed operation, passes through the pane 18 to the sample 34, and from the latter through the pane 18 into an incidence opening 38 of the camera 26. Only the light reflected therefrom indirectly, that is to say not at the specular angle, passes again through the pane 18 and into the incidence opening 38 of the camera 26. The second light source 24 is a white light-emitting diode (LED), or a number of light-emitting diodes of different colour (red, green, blue) which together supply white light or light of selectable colour. The selection between the pulsed operation and the continuous light mode can be performed via a switch (not shown) fitted outside on the housing, or via a bus which is connected to the evaluation device 28 and to an operator input device (not shown), or via a plug-in connection between the evaluation device and a harvesting machine (see FIGS. 4 and 5) which provides information as to whether a pulsed operation or a continuous light mode is required. It would also be conceivable for the operating mode of the second light source 24 to be automatically selected: firstly, the continuous light mode is selected. If it supplies fuzzy images, something which indicates a moving sample 34, the pulsed operation is automatically selected.

The camera 26 is of conventional design and comprises an objective 52 arranged at the incidence opening 38, a two-dimensional image sensor 54 and, if appropriate, a shutter (not shown). Such cameras are commercially available as television or digital cameras for still or moving images, and therefore require no further explanation.

The spectrometer 22 operates, in particular, in the near infrared region above approximately 950 nm, whereas the camera 26 is sensitive below this wavelength. The evaluation device 28 is connected to the image sensor 54 of the camera 38 and the detector elements 44 of the spectrometer 22 such that it can transmit signals. The evaluation device 28 further controls the second light source and can bring it into a flash operating mode or a continuous light mode. With the sample at rest, it is preferred to select the continuous light mode, while the flash operating mode is applicable to moving samples 34. Image processing software running in the evaluation device 28 identifies the boundaries of the particle of the sample 34 and determines the dimensions thereof therefrom. Moreover, possible impurities can be identified with the aid of the size, shape and/or colour. At the same time, the output signals of the detector elements 44 are evaluated in order to obtain sample parameters from the spectra, for example the content of certain constituent substances.

It would be conceivable for other applications to use the housing 12 in accordance with FIGS. 1 to 3, but to equip it only with a first light source 20 and a spectrometer 22, but not with a second light source 24 and not a camera 26. Similarly, the housing 12 could also be provided only with a second light source 24 and a camera 26, whereas the first light source 20 and the spectrometer 22 are eliminated. It would also be conceivable to allow only the second light source 24 to be eliminated for specific purposes; it is then possible, if appropriate, to bring the first light source 20 into a position which is situated between the light sources 20 and 24 in FIG. 2. It is possible in this way to use the same housing 12 for different measuring devices, and this simplifies the production and storage of the housing.

Figure 4:
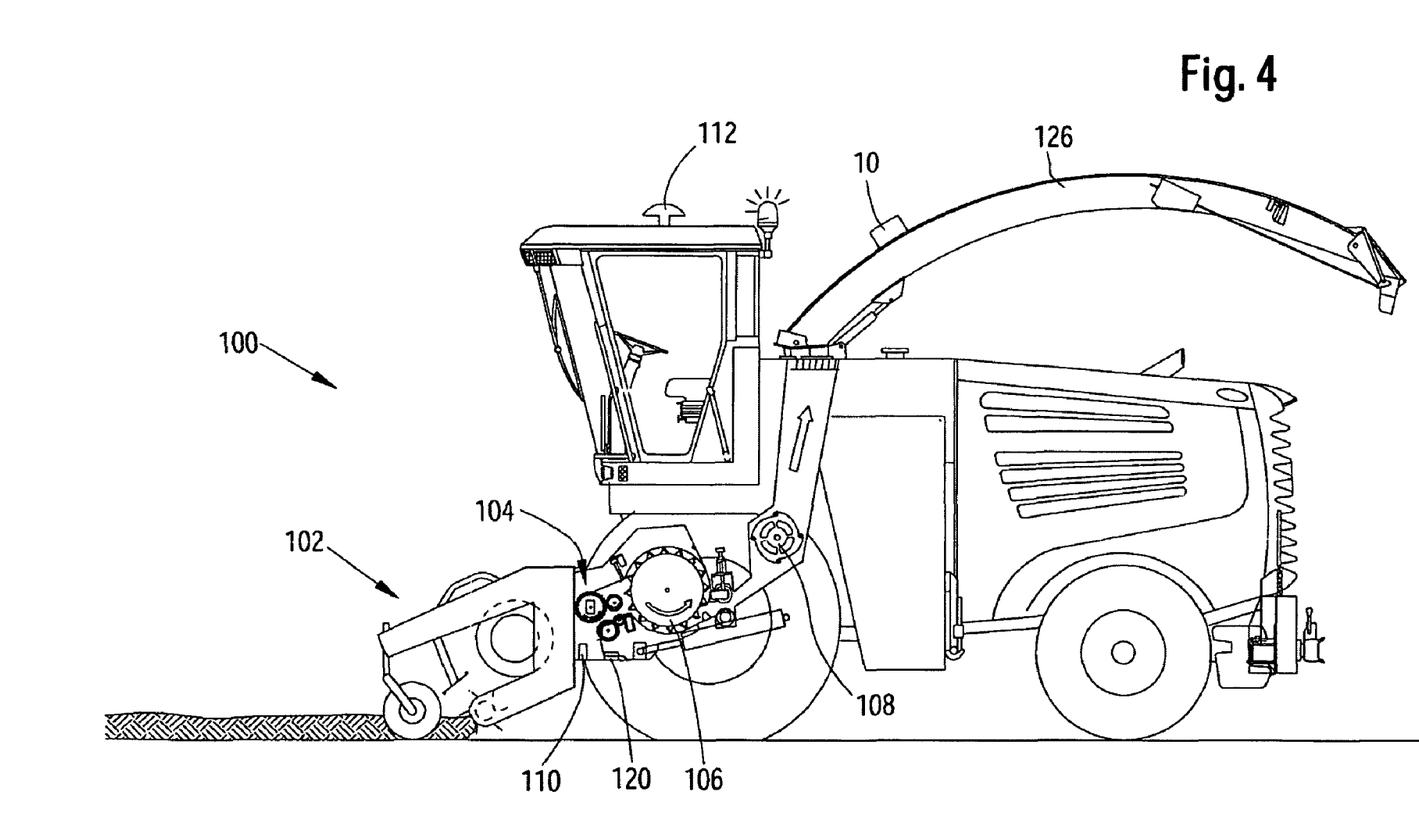
FIG. 4 shows a forage harvester with a measuring device.

The measuring device 10 can, for example, be fitted on a discharge device 126 of a harvesting machine in the form of a self-propelled forage harvester 100, as illustrated in FIG. 4. There, it cooperates through the pane 18, which is fitted in a suitable opening in the discharge device 126, with a sample 34 in the form of particles which consist of chopped harvest material, which have been picked up by a harvest material pickup device 102, fed by a feed device 104 to a chopping device 106, reduced in size there, and passed on by a fan 108 into the discharge device 126 and present themselves to the measuring device 10 in a free flow of harvest material.

The camera 26 of the measuring device 10 detects the pulsed light, reflected by the harvest material, from the second light source 24. The output signals of the image sensor 54 of the camera 26 are evaluated by the evaluation device 28 in order to determine the length of the particle of the sample 34 which corresponds to the cut length. If the cut length is greater than the image field of the camera 26, the cut edges can be identified with the aid of information relating to the average thickness of the harvest material and which is fed to the evaluation device 28. With the aid of the speed of the harvest material and the throughput, the evaluation device 28 can then evaluate the actual cut length. In another embodiment, the camera 26 is equipped with a shutter (not shown) which is so fast that the camera can take a sequence of images in the case of which the image contents adjoin one another. Owing to this overlapping, a virtual image can be produced in the direction of movement of the particle. In this image, the particle boundaries are identified and measured in order to determine the particle length. In both cases, the determined length of the particle is compared with a desired cut length and serves as feedback variable for controlling the conveying speed of the feed device 104 via a valve block which serves as actuator 110 and controls a hydraulic motor 120 for driving the feed device 104.

At the same time, the spectrometer 22 of the measuring device 10 detects spectral properties of the harvest material. The evaluation device 28 derives material parameters such as constituent substances and moisture content of the harvest material from the signals of the detector elements. The material parameters are stored electronically in a map in conjunction with an item of position information which is provided by a receiving antenna 112 of a satellite-based position determination system.

The material parameters determined by the evaluation device 28 can be checked or corrected with the aid of the output signals of the camera 26, and so it is possible, for example, to identify relatively large impurity fractions and to reject or correct associated material parameters, or the output signals of the camera 26 are used to identify the type of harvest material and this, in turn, is incorporated into the conversion of the spectra into material parameters.

Figure 5:
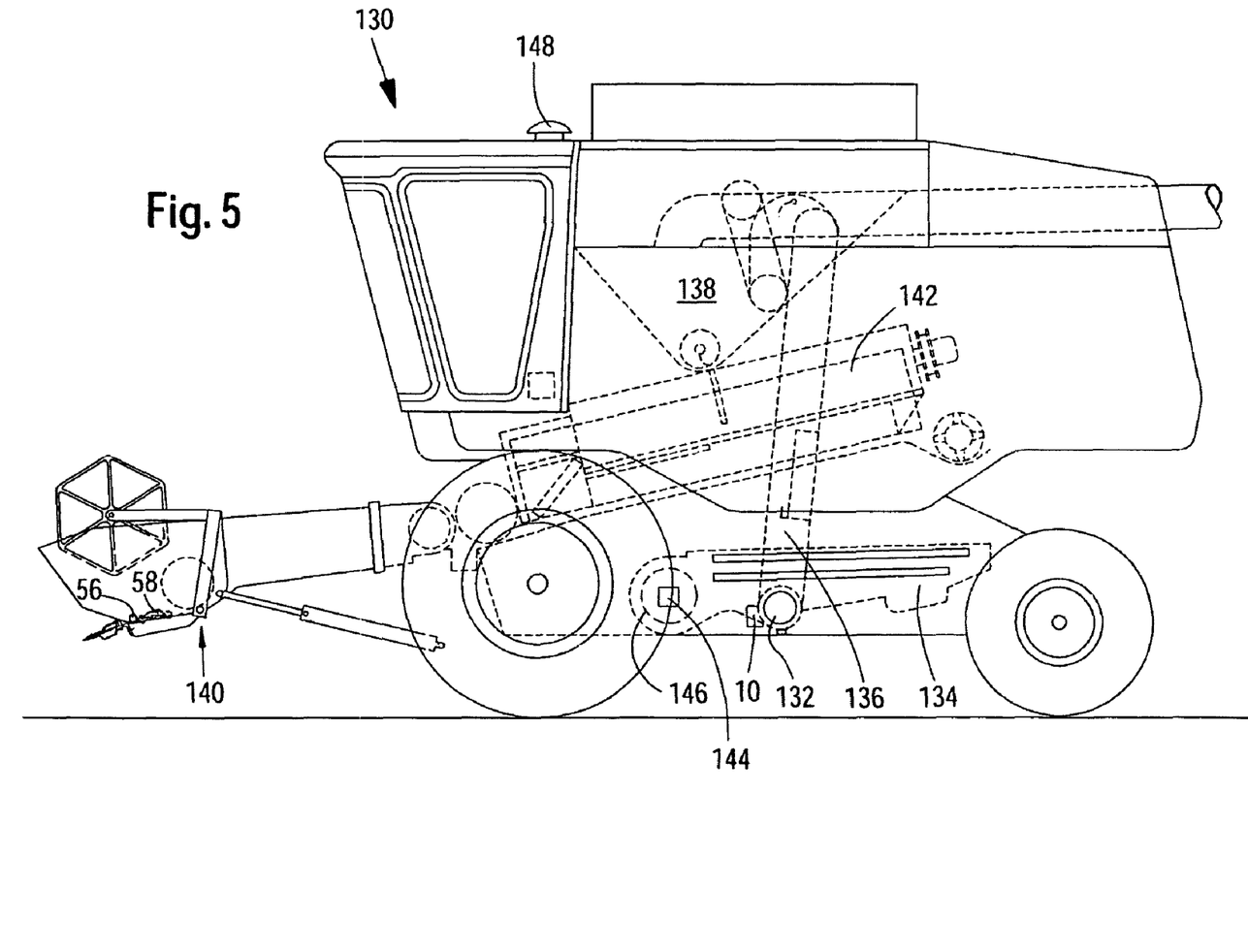
FIG. 5 shows a combine harvester with a measuring device.

FIG. 5 shows a harvesting machine in the form of a self-propelled combine harvester 130. The measuring device 10 is fitted on the wall of a cross-conveyor worm 132, and cooperates through an opening in the wall with the cleaned harvest material (grains) which is output by a cleaning device 134 and is passed on by the cross-conveyor worm 132 to a grain elevator 136 which deposits it in a grain tank 138. The cleaning device 134 receives the harvest material from a harvest material pickup device 140 which feeds it to a threshing and separating unit 142.

With the aid of the signals of the image sensor 54 and after evaluation by means of image processing software, the evaluation device 28 of the measuring device 10 identifies the fraction of impurities (for example chaff) in the flow of grain conveyed by the cross-conveyor worm 132, and the fraction of brokens there. The identified fraction of impurities serves for controlling an electric motor 144 which drives a fan 146 of the cleaning device 134. It is possible in this way to drive the fan 146 at a speed which provides an appropriate fraction of impurities in conjunction, likewise, with appropriate losses. Alternatively, or in addition, the opening size of the sieve can be automatically adjusted by an assigned actuator (not shown) with the aid of the determined fraction of impurities. Again, the image processing software can be used to determine the fraction of brokens, which is used to control the concave gap, and/or can serve, alongside the throughput and/or the grain loss, as a further parameter for determining the advancing speed.

The spectrometer 22 of the measuring device 10 supplies other harvest material parameters such as protein content, starch content, oil content and moisture content which are stored in a map in common with an item of position information which is provided by a receiving antenna 148 of a satellite-based position determination system. The fraction of brokens and impurities detected by the camera 26 is used in the evaluation device 28 to correct the errors in the calculated harvest material parameters. The algorithm for calculating error correction is determined empirically in advance (by experiments) and a type of family of characteristics is set up and stored in the evaluation device (28). This family of characteristics serves the evaluation device as a basis for calculating the error correction.

The invention claimed is:

1. A measuring device for optical and spectroscopic examination of a sample, the device comprising:
    a housing;
    a first light source arranged in the housing;
    a window fitted in a wall of the housing and having a transparent pane which is arranged in such a way that light from the first light source can fall onto a sample arranged outside the housing;
    an optical spectrometer arranged in the housing and having a dispersive element and a number of detector elements which optical spectrometer can record light from the first light source which is indirectly reflected by the sample and re-enters the housing through the window;
    an electronic camera which is arranged in the housing and whose incidence opening is directed onto the sample, through the window; and
    an electronic evaluation device which is connected to an image sensor of the camera and to the detector elements;
    where a second light source is arranged in the housing and is arranged in such a way that light from the second light source can fall onto the sample through the window,
    and where the camera is arranged in such a way that it can record light from the second light source which is reflected by the sample and re-enters the housing through the window, and
    wherein the first light source and the spectrometer are arranged diametrically opposite an optical axis of the window, in that the second light source and the camera are likewise arranged diametrically opposite the optical axis of the window, and in that the first light source and the second light source are arranged angularly offset in relation to the optical axis of the window.

2. The measuring device according to claim 1, wherein the first light source can emit continuous light.

3. The measuring device according to claim 1, wherein the electronic evaluation device is configured to evaluate the length of particles of the sample.

4. The measuring device according to claim 3, wherein the electronic evaluation device is configured to evaluate the length of particles of the sample by carrying out a statistical analysis while considering information fed to it with regard to the speed of movement of the particles and the size of the particles and a visible number of the intersection edges which is evaluated with the aid of an image evaluation of the image sensor signals of the camera.

5. The measuring device according to claim 3, wherein the electronic evaluation device is configured to evaluate the length of particles of the sample by combining a number of images of the camera recorded sequentially in time and in the case of which the contents of the image adjoin one another.

6. A measuring device for optical and spectroscopic examination of a sample, the device comprising:
    a housing;
    a first light source arranged in the housing;
    a window fitted in a wall of the housing and having a transparent pane which is arranged in such a way that light from the first light source can fall onto a sample arranged outside the housing;
    an optical spectrometer arranged in the housing and having a dispersive element and a number of detector elements which optical spectrometer can record light from the first light source which is indirectly reflected by the sample and re-enters the housing through the window;
    an electronic camera which is arranged in the housing and whose incidence opening is directed onto the sample, through the window; and
    an electronic evaluation device which is connected to an image sensor of the camera and to the detector elements;
    where a second light source is arranged in the housing and is arranged in such a way that light from the second light source can fall onto the sample through the window,
    and where the camera is arranged in such a way that it can record light from the second light source which is reflected by the sample and re-enters the housing through the window,
    wherein the second light source can be operated in a pulsed operation.

7. The measuring device according to claim 6, wherein the second light source comprises a flash lamp and/or a light-emitting diode.

8. A measuring device for optical and spectroscopic examination of a sample, the device comprising:
    a housing;

a first light source arranged in the housing;
a window fitted in a wall of the housing and having a transparent pane which is arranged in such a way that light from the first light source can fall onto a sample arranged outside the housing;
an optical spectrometer arranged in the housing and having a dispersive element and a number of detector elements which optical spectrometer can record light from the first light source which is indirectly reflected by the sample and re-enters the housing through the window;
an electronic camera which is arranged in the housing and whose incidence opening is directed onto the sample, through the window; and
an electronic evaluation device which is connected to an image sensor of the camera and to the detector elements;
where a second light source is arranged in the housing and is arranged in such a way that light from the second light source can fall onto the sample through the window,
and where the camera is arranged in such a way that it can record light from the second light source which is reflected by the sample and re-enters the housing through the window,
wherein the electronic evaluation device is configured to use image sensor signals on the camera to check to correct parameters of the sample with the aid of the output signals of the detector elements of the spectrometer.

9. A self-propelled harvesting machine comprising:
a housing;
a first light source arranged in the housing;
a window fitted in a wall of the housing and having a transparent pane which is arranged in such a way that light from the first light source can fall onto a sample arranged outside the housing;
an optical spectrometer arranged in the housing and having a dispersive element and a number of detector elements which optical spectrometer can record light from the first light source which is indirectly reflected by the sample and re-enters the housing through the window;
an electronic camera which is arranged in the housing and whose incidence opening is directed onto the sample, through the window; and
an electronic evaluation device which is connected to an image sensor of the camera and to the detector elements;
where a second light source is arranged in the housing and is arranged in such a way that light from the second light source can fall onto the sample through the window,
and where the camera is arranged in such a way that it can record light from the second light source which is reflected by the sample and re-enters the housing through the window, and
wherein the first light source and the spectrometer are arranged diametrically opposite an optical axis of the window, in that the second light source and the camera are likewise arranged diametrically opposite the optical axis of the window, and in that the first light source and the second light source are arranged angularly offset in relation to the optical axis of the window.

10. The harvesting machine according to claim 9, wherein the harvesting machine comprises an actuator which is connected to the electronic evaluation device and is intended for controlling a parameter of the harvesting machine as a function of properties of harvest material which are determined by the electronic evaluation device.

11. The harvesting machine according to claim 9, wherein the housing is arranged downstream of a cleaning device of a combine harvester, in that the camera cooperates with image processing software in the evaluation device which is configured to detect at least one of a fraction of impurities or broken grain in the flow of grain observed by the electronic evaluation device, and in that the evaluation device is configured to use the fraction determined by the image processing software to correct parameters of the grains, detected with the aid of the spectrometer, doing so on the basis of a family of characteristics stored in the evaluation device and based on one or more experiments.

12. The harvesting machine according to claim 11, wherein the parameters of the grains include one or more of the following: protein content, starch content, oil content or moisture content.

* * * * *

UNITED STATES PATENT AND TRADEMARK OFFICE
CERTIFICATE OF CORRECTION

PATENT NO. : 7,804,588 B2
APPLICATION NO. : 11/972104
DATED : September 28, 2010
INVENTOR(S) : Kormann et al.

It is certified that error appears in the above-identified patent and that said Letters Patent is hereby corrected as shown below:

Title page, item (73) - add further assignee "Carl Zeiss Jena GMBH, Jena, Germany"

Signed and Sealed this
First Day of February, 2011

David J. Kappos
*Director of the United States Patent and Trademark Office*